United States Patent [19]
Mykietiuch

[11] Patent Number: 4,949,713
[45] Date of Patent: Aug. 21, 1990

[54] TENSILE ARC AND BRIDGE BODY SUPPORT

[76] Inventor: Walter Mykietiuch, 21012 Royal Ann Rd., Bothell, Wash. 98021

[21] Appl. No.: 916,898

[22] Filed: Oct. 8, 1986

Related U.S. Application Data

[63] Continuation-in-part of Ser. No. 642,107, Aug. 20, 1984, abandoned.

[51] Int. Cl.$^5$ ............................................. A61F 5/01
[52] U.S. Cl. .................................... 128/78; 128/845; 128/870; 128/168
[58] Field of Search ............... 5/89, 82 B, 83, 85, 5/82 R; 128/80 R, 132 R, 149, 133, 134, 168; 287/464, 458, 459; 182/6, 7

[56] References Cited

U.S. PATENT DOCUMENTS

| | | | |
|---|---|---|---|
| 1,450,950 | 4/1923 | Jenkins | 5/89 X |
| 2,279,694 | 4/1942 | Martinson | 5/82 |
| 2,600,944 | 6/1952 | Sam | 297/423 |
| 2,826,245 | 5/1958 | Sellner | 160/DIG. 15 |
| 3,585,639 | 6/1971 | Enicks | 128/132 R |
| 3,754,786 | 8/1973 | Boucher | 297/56 X |
| 3,859,677 | 1/1975 | Nordwig | 5/82 X |
| 3,999,227 | 12/1976 | Ingemansson | 5/89 X |
| 4,070,721 | 1/1978 | Stasko | 5/89 |
| 4,221,011 | 9/1980 | Finchbaugh | 5/89 |
| 4,295,683 | 10/1981 | Dubbink | 297/458 X |
| 4,367,897 | 1/1983 | Cousins | 297/458 |
| 4,510,888 | 4/1985 | DeAngelis | 128/132 R |

FOREIGN PATENT DOCUMENTS

| | | | |
|---|---|---|---|
| 333129 | 10/1958 | Switzerland | 160/DIG. 15 |
| 1208140 | 10/1970 | United Kingdom | 160/DIG. 15 |

*Primary Examiner*—Robert A. Hafer
*Assistant Examiner*—Kevin G. Rooney

[57] ABSTRACT

An individually fitted apparatus for, and method of supporting an individual by, a tensile arc and bridge body support, comprising in combination; A fitted tubular frame outlining the immediate periphery of each supported body portion and attached to the frame is a fabric that is deeply and tightly contoured to the three-dimensional profile of the body portions. The fabric extends down a side of each body portion curves and passes under, and up to the other side. A contoured rigid member is attached to the fabric that opposes a planar or concave surface of the body portions, such as the back of the torso. By suspending the individual in this support, the tensile fabric applies pressure to the convex curves of the body portions and the contoured bridge applies pressure to the planar or concave surfaces. The support surface area can be increased substantially by using this support and the support pressure would drop accordingly.

5 Claims, 4 Drawing Sheets

TENSILE ARC AND BRIDGE BODY SUPPORT

This application is a continuation-in-part of Ser. No. 06/642,107 filed Aug. 20, 1984, now abandoned.

The following represents the state of the art of which applicant is aware, insofar as these patents are germane to the process at hand.

Patent references from prior application:
U.S. Pat. No. 85,363 Buckel, Dec. 29, 1868
U.S. Pat. No. 2,285,925 Handy, June 9, 1942
U.S. Pat. No. 2,600,944 Sam, Jun. 17, 1952
U.S. Pat. No. 2,826,245 Sellner, Mar. 11, 1958
U.S. Pat. No. 3,428,973 Hargest et al, Feb. 26, 1969
U.S. Pat. No. 3,585,639 Enicks, Jun. 22, 1971
U.S. Pat. No. 3,754,786 Boucher et al, Aug. 28, 1973
U.S. Pat. No. 3,949,435 Dionne, Apr. 13, 1976
U.S. Pat. No. 3,999,227 Ingemansson, Dec. 28, 1976
U.S. Pat. No. 4,070,721 Stasko, Jan. 31, 1978
U.S. Pat. No. 4,221,011 Flichbaugh, Sep. 9, 1980
U.S. Pat. No. 4,295,683 Dubbink et al, Oct. 20, 1981
U.S. Pat. No. 4,301,791 Franco III, Nov. 24, 1981
U.S. Pat. No. 4,367,897 Cousins, Jan. 11, 1983
U.S. Pat. No. 4,510,888 DeAngelis et al, Apr. 16, 1985
Patent made of reference for the current application:
U.S. Pat. No. 1,326,530 Radcliff, Dec. 30, 1919
U.S. Pat. No. 1,557,647 Austin, Oct. 20, 1925
U.S. Pat. No. 3,011,826 Bowring et al, Dec. 5, 1961
U.S. Pat. No. 3,278,230 Boyce et al, Oct. 11, 1966

The application for the present invention entitled the "Tensile Arc and Bridge Body Support" is a continuation in part application of the previous patent application entitled "Hypercontoured Suspended Supporting Apparatus", Ser. No. 642,107, Filed Aug. 20, 1984.

BACKGROUND OF THE INVENTION

This invention relates to improved body supports with medical and aerospace applications. Medically, these support configurations will help protect against and treat bed sores. These supports will also help reduce the discomfort associated with prolonged immobile situations and also will immobilize injured patients and thus prevent patients from further injuring themselves. In the aerospace field these support configurations will protect pilots against the high acceleration and vibration forces found in high performance aerospace vehicles.

Medical Field: Bed sores are caused primarily by pressure. Other causative factors include moisture build up and adverse skin temperature gradients. When conventional supports such as chairs, wheelchairs and beds are used, boney prominences are exposed to the highest degree of pressure and they are most susceptible to skin breakdown.

Many have attempted to redistribute pressure evenly so as to reduce the excessive pressure under boney prominences. These devices include cushion-like pads that are foam, gel, water, air or sand filled. Other devices alternate pressure such as an alternating pressure pad or beds which tilt the patient from side to side.

Many devices mentioned above, have surfaces that lack sufficient porosity, which then cause an excessive build-up of moisture against the skin. Foam and air-filled cushions lack air circulation and possess high insulating properties, both of which lead to an excessive rise in skin temperature. On the other hand, water-filled beds and cushions conduct heat away from the skin, thereby adversely reducing skin temperature. Air, water, gel and sand filled devices may leak once punctured and thus loose their effectiveness and become hazardous. Another problem associated with the above supports includes the inability to provide a safe, practical and stable support that prevents excessive patient movement while on the support. A still further problem with these supports is that they do not provide a stable support surface while transferring onto or off of these supports.

Aerospace Field: Aerospace pilots are exposed to the stress of high acceleration, impact acceleration and vibration forces. These stresses overcome the body's elastic tissue's ability to keep the body from deforming under the increased hydro-static pressure and increased weight. Rigid contoured couches, hard shell suits, water tanks, anti-"G" suits and Bowring et al (U.S. Pat. No. 3,011,826) net crew seat have been developed to better protect pilots. Bowring's support has been found to be effective in helping pilots withstand high acceleration forces. However, Bowring's support has a serious rebound problem. This rebound effect occurs because the pilot sinks in the seat during acceleration and when the acceleration stops the pilot is thrown out or rebounds out of the seat due to the recovery of the yieldable resilient support fabric. A further disadvantage is that the support is not multi-directional, it only provides support from front to back (eye balls in). Bowring's support does not protect against side to side movement, nor does it protect against back to front movement (eye balls out). A still further disadvantage is that the depth of the pilot in the seat changes significantly as the acceleration forces change.

Field of Sling Supports: Sling supports like Sam's seat device U.S. Pat. No. 2,600,944, Dionne's torso support U.S. Pat. No. 3,949,435, Bowring's net crew seat, and Dubbink's bathing chair U.S. Pat. No. 4,295,683 do not have an individually fitted frame and supporting fabric for different length and width bodies and thus physiologically critical protection against pressure is not achieved. Moreover Bowring's and Dubbink's devices are shallow supports and do not redistribute support pressure to a significant portion of the sides of the body portions. A further disadvantage of all these sling supports is that a person would have to enter these supports vertically, like in a normal seat or bed. Thus transferring into or out of these supports would be very difficult for healthy people and would be impossible and potentially injurious to most patients. A still further disadvantage is that a person's legs are either seriously squeezed together as in Dionne's support, or kept physiologically too close together thus causing contraction of the patient's legs as in Sam's device, or as in Bowring's net crew seat keeping the legs too close together in an non-optimal position.

OBJECTS AND SUMMARY OF THE INVENTION

Accordingly, the primary objective of the present invention is to protect a body against physiologically damaging pressure caused by gravity.

It is a concurrent object to provide a body support that redistributes support pressure over the largest body surface area that is practically possible.

It is also a concurrent object to provide a support material which functions dynamically with the body, much like a fluid.

It is also a concurrent object to provide a device that is individually fitted to different size people.

It is a further object to provide stability and ease while sitting, reclining, lying or when one is transferred into or out of the present invention.

It is a further object to provide a device which is capable of supporting a body in multi-directions.

It is a still further object to immobilize or restrain a person and thus prevent excessive movement that might cause injury or might complicate preexisting injuries.

It is a further object to support each individual body portion in a natural or most physiologically beneficial angle in relation to all of the other body portions.

It is a further object to provide a device which controls skin moisture.

It is a still further object to provide a device which maintains and controls proper skin temperature.

It is a further object to provide a support material that is removable and launderable.

It is a further object to provide a device which is capable of administering hyperbaric oxygen directly to the skin surface that the body is lying on and also to the entire body.

It is a further object to provide monitoring devices through the support material.

It is a further object to provide openings through the support material for the purposes of evacuating bodily wastes.

It is a further object to provide a support which improves the resistance of aerospace pilots to the pressure stresses of high acceleration and vibration environments and also to eliminating the rebound effect of resilient supports.

It is a still further object of the present invention to increase comfort and safety by addressing all of the above needs.

These and other objects will be made manifest when considering the following detailed specification when taken in conjunction with the appended drawing figures wherein there has been provided a structure to contour the support surface so as to maximize the skin contact area and thus, redistribute support pressure onto the sides of each supported body portion. To understand the principle of the present invention there needs to be an understanding of the dynamic forces acting on a body floating in a fluid. A body portion floating in a fluid will have the constant force of the fluid applying constant pressure to the sides and underneath. This force which supports the body is hydro-static pressure. Because the pressure is applied to a large surface area (sides and underneath), the highest pressures are lower than would be had the body been supported mainly from underneath. Although fluid filled devices contour around a body portion the tension in the material enclosing the fluid prevents the fluid and material from contacting a large surface area of the sides of the body portion and thus, from applying significant pressure to the sides. These devices still support mainly from underneath the body. Some sling supports contour around the sides of a body, however, they do not apply significant pressure to the sides or apply too much pressure on the sides and not enough underneath the body.

The instant invention attempts to provide a practical, safe, and effective device which simulates a hydro-static force over the maximum body surface area possible, (sides and underneath), thereby lowering significantly the highest support pressures. This is made possible by the tensile arc and bridge body support. This apparatus is comprised in combination of the following;

A fitted apparatus that supports all or some of an individual's body portions that are weight bearing. That is, it is adapted to support the legs and seating area of an individual who is seated, or it is adapted to support the legs, torso, arms, and head for a person lying down or any one part or combination of the above.

The apparatus has a frame member made of a rigid tubular material that is supported and elevated off a base surface, such as above a bed, chair or the like, by rigid vertical members. The tubular frame member is located above and adjacent to, but remote from, each side of the supported body portions. The frame member, also, extends the length and width of each body portion. This frame is shaped to fit different sizes and/or made adjustable to conform to the size and shape of the selected body portions.

Attached to the rigid frame is a coextensive flexible material that is tailored in different sizes to fit deeply and tightly to the three-dimensional profile of the length and width of the selected body portions. The vertical sides of the contoured fabric are attached to the fabric supporting frame above. The fabric extends down from the frame, curves down and passes under the body portion, and curves and extends up the other side, to be attached to the frame there as the said first side. Thus forming the deep, tight, three-dimensional contour.

The framing and the fabric is dimensioned to support and suspend the body portions off the base surface.

Should the curves along the sides of the body turn into a plane, as it does on the front and back of the torso, a rigid contoured bridge would be attached to the fabric to span the plane. This bridge is required because without it the torso would collapse convexly into one continous arc from one side of the torso to the other. Generally, uniform pressure is exerted on a circular object like a leg or an arm with the use of a tensile arc support. However, a tensile material around a circular object with a planar or concave surface will apply excessive pressure on the curved surface and almost no pressure on the planar or concave surface. Since the body is elastic, the weight of it along with the lack of pressure from the unbridged tensile material underneath causes the torso to collapse into one continous arc.

It is important to note that the fabric on the sides of the body portions is in contact with most of the side surface area (as opposed to partial contact), of the body portion. Also, most importantly, a body portion placed in this support is exposed to a dynamic force similar to hydro-static pressure. When a body portion is placed inside the tensile arc and bridge support the fabric on the sides of the body portion moves inward with a constant force and since the fabric is already in contact with the sides of the body, the constant inward force translates into a constant pressure against the sides of the body portions. This redistributes and lowers the support pressure. The tension in the fabric and the pressure moving inwards is directly proportional to the weight of the body. A simple example to illustrate the above effects would be, to support a rope at both ends and let it dangle loosely in an arc, then place a weight in the middle of the arc. The result would be that the rope on either side of the weight would move closer together with a force proportional to the weight. The use of this design to effect a dynamic action for the purposes of redistributing pressure over the maximum body surface contact area is the principle of the tensile arc and bridge support.

The air or liquid-filled devices provide a dynamic support which moves with the patient. However, these air and fluid supports are unstable when transferring patients to and from them. Once on these devices, the air or fluid moves too freely, thereby causing disorientation of the patients, also, as wheelchair cushions they are more unstable during wheelchair propulsion. The present invention inherently provides a dynamic support which also moves with the patient. However the structure is sufficiently stable, unlike fluids, to support the patient securely and also to provide stability during wheelchair propulsion. Also, easy, safe, horizontal patient transferring is provided by lowering the fabric support frame to a level generally flush with the base surface underneath the patient, i.e. bed, chair or the like.

The ability of a device to support a person and prevent side to side or head to toe movement of that person is important in areas where there has been an injury such as a spinal injury and when there is great need to immobilize the patient and prevent further injury. The present invention has some inherent restraining qualities. However, additional structures can be added to the support, to further stabilize and restrain the body. These additions will be described in FIGS. 2 through 6. The immobilization of a patient can be with a portable device that is somewhat adjustable to most patients as would be required in medical ambulance transport, and also, a device that is precisely adjustable as would be required in the long term care of injured patients in hospitals. Preventing side to side movement is also important when there is an additional need to tilt or rotate the patient from side to side for the purposes of stimulating the patient and further improving his physiological functioning. Multi-direction or 360 degrees of support protection can also be incorporated into the present design for supporting a person on his back, side or on his front.

A body floating in water takes on a natural, somewhat semi-recumbent position with the legs somewhat abducted. This too can be incorporated in the present design to maximize physiological functioning.

A porous fabric can be used which is permeable to air and body fluids, thus allowing the skin to breathe. This prevents moisture build-up next to the skin due to perspiration or other bodily fluids. Burn victims on the other hand may need an impervious support material instead. Excessively hot or cold skin temperatures are both uncomfortable and potentially damaging to the skin. The permeable fabric allows room temperature air to circulate to the patient's skin. Temperature can be more actively affected by the use of an insulating jacket underneath and around the patient. Further, a more active approach would be to use a cooling or heating system when required.

Many foam, air and sand filled devices cannot be cleaned easily. With the present invention, having a removable fabric allows for laundering as necessary. Also, there are no leakage problems due to puncturing as can happen in air and fluid filled cushion devices. If puncturing should occur, the integrity of the system is maintained since no air or fluid is required in the system. The present invention also eliminates the safety problem of slippery floors such as occurs when the above mentioned devices leak.

The strucures of the present invention allow for the administration of hyperbaric oxygen therapy, or other appropriate therapy, through the permeable fabric or through an opening in the fabric. The oxygen therapy can be applied to a small area including the person's skin surface in contact with the support material or enveloping the entire person. These structures allow for the monitoring of skin capillary blood flow, or any other type of monitoring, by attaching the monitoring device through the fabric or an opening in the fabric. Also, evacuation of bodily wastes can be carried out through openings in the support material.

Gravity causes excessive support pressure while on most previous devices, especially in the high acceleration or high gravity environments of aerospace travel. The only method that substantially cancels the effects of gravity is submersion or floatation in a fluid. This is impractical and unsafe. In a fluid, as the acceleration increases the body weight and the surrounding fluid weight increase simultaneously. No deformation or displacement of body tissue takes place because of the automatically counteracting pressure of the surrounding fluid. Similarly, the present invention reacts to changes in gravity. As the acceleration increases, the body weight increases, this causes a simultaneous increase in the tension of the fabric. Little body tissue deformation or displacement occurs because of the counteracting higher tension and pressure from the fabric. Naturally an extremely strong fabric and frame would have to be used in order to withstand these heavy loads. Also, to minimize the rebound effect, a fabric with the least resiliency would be used. A further advantage of this support is its ability to protect and support the person from acceleration forces acting from side to side, front to back and back to front.

DESCRIPTION OF THE PREFERRED EMBODIMENT

Figure 1:
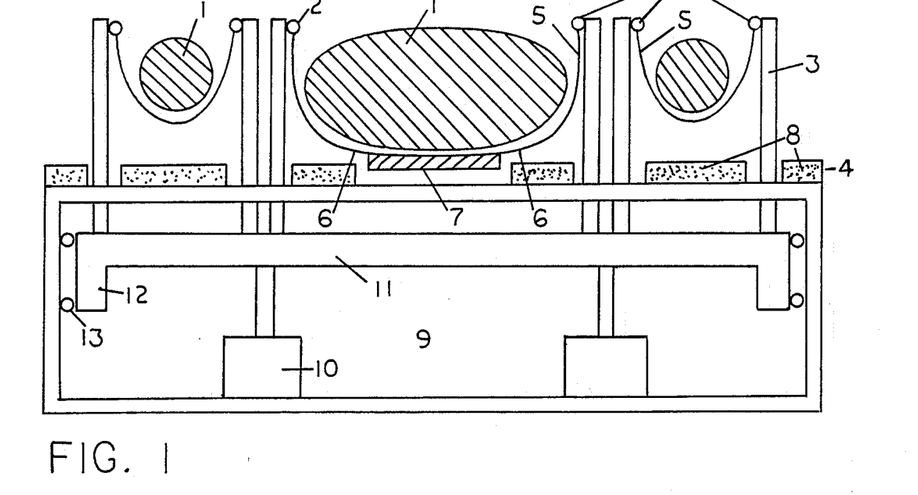
FIG. 1 is a cross sectional view of the width of a person's torso and the two arms and the section of the present invention supporting those body portions.

Referring to the drawings now wherein like reference numerals refer to like parts throughout the various drawing figures. FIG. 1 is a cross sectional view of the width of a body's torso and its two arms and the section of the framing and fabric supporting those body segments, and also the base structure 9 supporting both. A rigid frame 2 is supported above and on each side of each body portion by rigid vertical support members 3. The vertical support members are supported by a base structure 9. The rigid frame 2 is contoured or outlines the periphery of each body portion being supported. Noting the arms firs, the rigid frame 2 supports the flexible, permeable material 5, this fabric or material extends down a side of the arm, curves downward, under, and curves and extends up to the other side to be attached there to frame 2 as the said first side. Noting the torso now, the fabric supporting frame 2 again supports the fabric 5 on a side of the torso, extends down, curves under and levels to the plane of the person's back and then, extends up to the other side. As detailed before, a flexible material in tension around an object will put more pressure against the curved sides than the side or sides that are concave or planar. A rigid bridge spanning the plane area will equalize the pressure more evenly between the sides and the back. Therefore a rigid bridge 7 is attached to the fabric 2 to span the plane between the two curves 6 of the torso.

In order to facilitate patient transfer, the entire framing and bridge structure above the base surface 4 can be lowered to a position generally flush with the base surface 4. The base surface has a vinyl coated cushion 8, approximately two inches thick, that has channels cut into appropriate areas to receive the framing and bridge structure. The vertical frame supports 3 pass through openings in the base surface and into the base compartment 9. The vertical frame supports 3 are attached to and supported by a foundation 11. This foundation is supported by and attached to a lifting mechanism 10. The lifting mechanism shown is a hydraulic one, but it can easily be substituted by any other appropriate lifting mechanism. To stabilize and smooth out the level changes of the foundation 11, a rigidly connected member 12 is located at each end of the foundation 11. Attached to member 12 are wheels 13 in order to reduce the friction of up and down movement. The opposite method of mating the support frame 2 with the base surface 4, is to make the body framing stationary and instead have the base unit 9 movable up and down. The entire structure of FIG. 1 can be placed on another substructure, not shown, that would mechanically tilt or rotate the patient from side to side. The tilting would stimulate the circulatory and other bodily systems and thus further improve the benefits to the patient.

Figure 2:
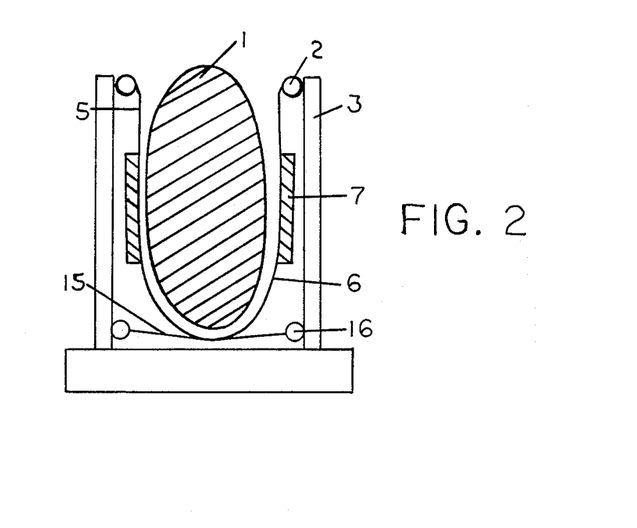
FIG. 2 is a simplified cross sectional view of the width of a body's torso supported on its side.

FIG. 2 shows a simplified cross sectional view of a body's torso supported on its side. Again the vertical frame members 3 supports frame member 2 which supports the fabric 5. The fabric 5 attached to the frame 2 extends down across a large plane along the back, and along the front of the torso. Without the two rigid bridges 7, a simple sling would concentrate most of the support pressure underneath the torso. Attaching the two bridges to the fabric in order to span the planes of the torso, will reduce significantly the pressure underneath the torso and redistribute it to the sides of the torso.

FIG. 2, in addition, shows a stabilizing member 15 made out of a flexible fabric that is sewn to the bottom middle section of the fabric member 5, the two ends of member 15 are attached to a rigid frame 16. Both the fabric member 15 and rigid frame member 16 extend the entire length of the body portions. The stabilizing member 15 prevents the side to side movement of the torso and also allows for the entire structure of FIG. 2 to be tilted at an angle of up to approximately 50 degrees to either side and still adequately support the patient.

Figure 3:
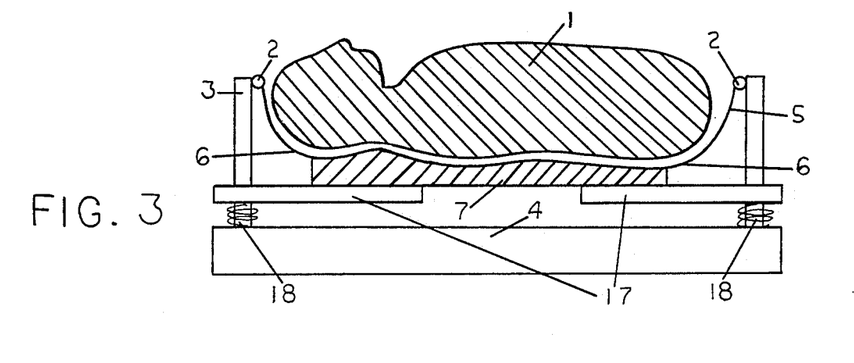
FIG. 3 is a cross sectional view of the profile of the head, neck, and torso of a body supported in the supine position.

FIG. 3 shows a cross sectional view of the profile of a body's head, neck and torso and the section of the present invention supporting those body parts. The legs are not needed to be shown. Again as before, the vertical member 3 supports member 2 and member 2 supports the fabric 5. Again too, the planar surface between the curves at the base of the head 6 and the curve near the coccyx 6 are bridged by a rigid contoured bridge 7. Rigid stabilizing members 17 are attached to the bridge 7 and extend to and around vertical support members 3. The member 17 functions like stabilizing member 15 of FIG. 2, however, in FIG. 3 a rigid stabilizing member would be more appropriate. Vertical member 3 passes through a hole in members 17, although they are in contact with each other they are not attached to each other. This allows for the automatic leveling of the bridge 7 and framing members 2 when the patient support frame 2 is lowered to a position generally flush with the base surface 4. Also, wrapped around vertical member 3 is a compression spring 18, that can be added as required. The spring 18 can be used to relieve some of the tension in the torso supporting fabric 5 in effect becoming a secondary supporting means for the torso. The torso has a disproportionately higher weight to side surface area ratio than the legs or arms, this causes the tension in the fabric to be greater in the torso than in the arms or legs. The use of the compression spring 18 helps equalize this tension differential.

Figure 4:
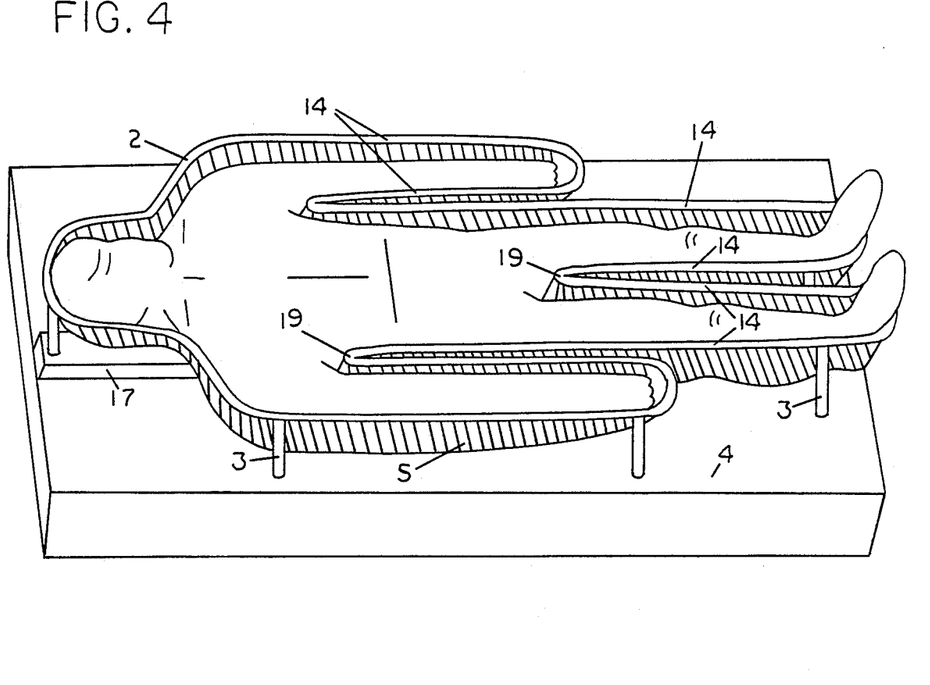
FIG. 4 is a perspective view of the apparatus of FIGS. 1 and 3.

FIG. 4 shows a perspective view of a body being supported in a recumbent position. Simply, the base 4 supports the rigid vertical members 3 and they in turn support the rigid frame members 2. As can easily be seen, the framing members 2 extend the length and width of each body portion forming one coextensive continuous frame. The frame 2 supports the fabric 5 which is contoured to the three-dimensional profile of the person's back and is also contoured to the outline of the front of the person. Thus, all sides of each body portions are supported. The fabric supporting frame 2, at the armpit and groin area 19 also is located above, and is adjacent to, the sides of those body sections. As shown in FIG. 3, stabilizing members 17 are used to prevent the patient's weight from moving the support fabric 5, and thus itself, from side to side and from head to foot.

For burn injured patients, the support fabric 5 can be impervious, to minimize body fluid loss through the skin. Also, the framing structure 2 outlining the body, can be wider than the body portions and still be adequate for supporting the patient under low uniform pressure. For injuries such as spinal cord injuries, the fabric chosen would be permeable in order to minimize perspiration and discomfort. For both patient types, a resilient elastic-like material could be used to further improve comfort and fit. In addition the support fabric 5 can have a padded or fur-like lining.

Although the support structure in FIG. 4 shows a level recumbent body in a planar frame, it will be understood that this support can be adapted with hinged members, not shown, at the joint locations of the body such as shown by reference numbers 14. This would further add to the comfort and needs of the patient.

Figure 5:
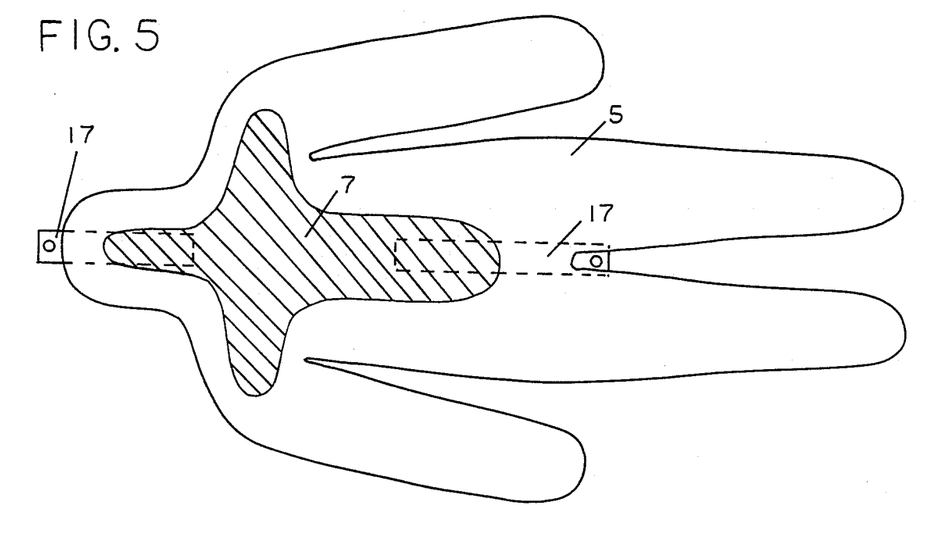
FIG. 5 is a simplified view from the top of the support of FIG. 4 without the body and showing a cross shaped bridge network.

FIG. 5 shows a view from the top of the recumbent body support of FIG. 4. The rigid bridge network 7 spans the planes of the torso. This bridge network spans the width of the torso, wider across the width of the shoulders and longest across the plane approximately between the base of the head and the coccyx. This bridge network 20 thus forms one coextensive cross-shaped rigid bridge that is attached to the support fabric 5. Below the bridge network is the stabilizing members 17. At each end of the stabilizing members, the vertical members 3 pass through and function as guides to keep the stabilizing members in alignment.

Figures 6, 7, 8, 9, 11:
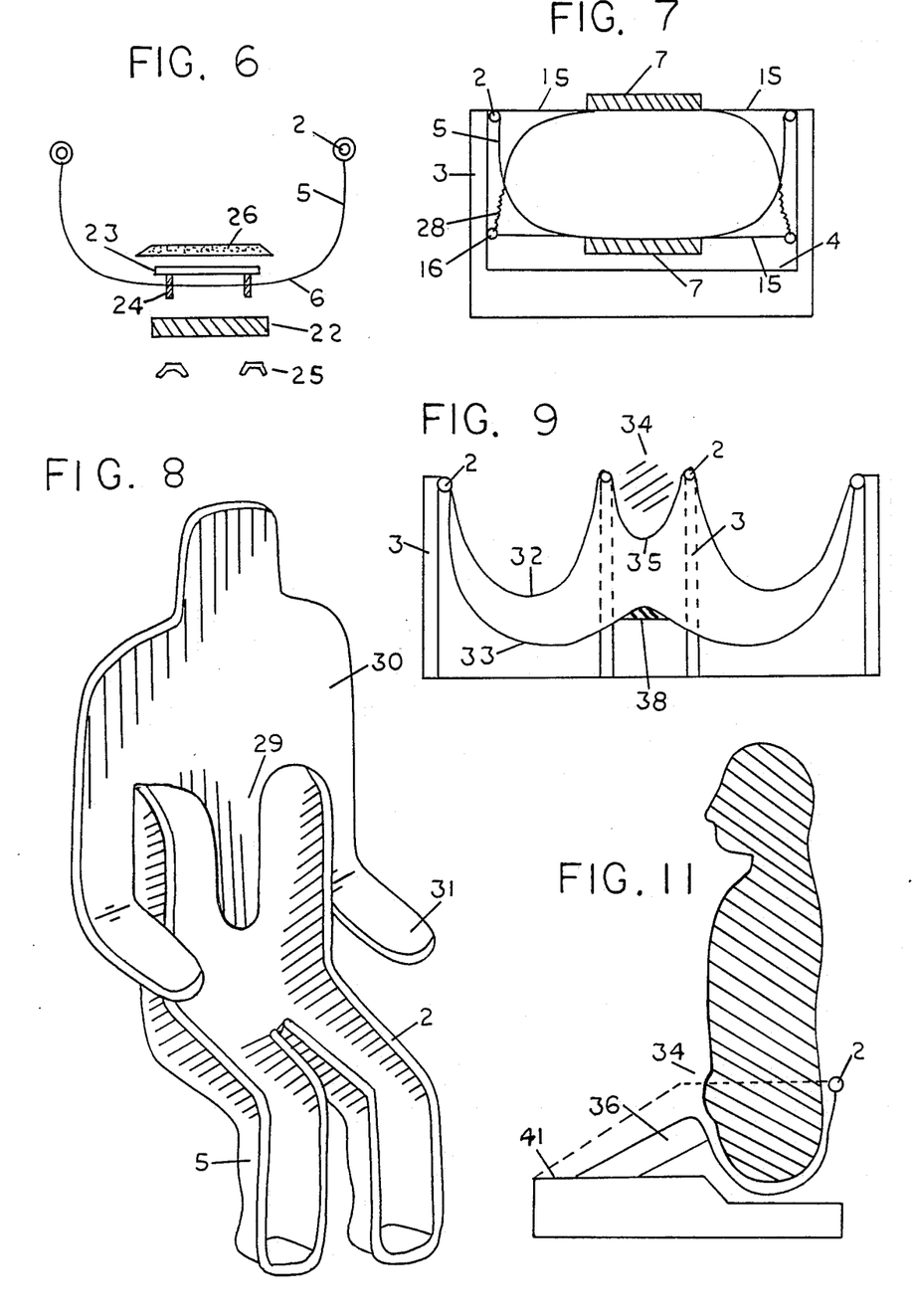
FIG. 6 is a exploded cross sectional view of the torso support shown in FIG. 1, with the bridge spanning the plane of the torso and its method of attachment to the fabric.
FIG. 7 is a cross sectional view of the width of a torso being supported in a version of the present invention that can support a body in 360 degrees direction.
FIG. 8 is a simplified perspective view of a chair version of the present invention.
FIG. 9 is a front cross sectional view of the buttocks and groin area of the structure shown in FIG. 8.
FIG. 11 is a profile view of the outline of support provide in the structure of FIG. 10.

FIG. 6 is a cross sectional view of the torso support of FIG. 1, 3, 4, and 5 and the method of attaching the bridge to the fabric. The bridge 22 is composed of any suitable rigid lightweight material that is located underneath the plane of fabric 5, above the fabric is a very thin rigid material with threaded bolts fastened to its outside periphery. The bolts of the top thin plate 23 pass through holes in the support fabric 5, and through holes in the bridge 22 below. Wing nuts 25 are then threaded and tightened onto the bolts 24. This sandwiches the fabric between the plate 23 and the bridge 22. As can be observed, the width of the bridge member 22 can be much greater than the width of the plane, for it is the width of the top plate 23 that needs to precisely fit the span of the plane. On top of the thin plate 23 a thin cushion material is attached. The entire bridge network, including the cushion material 26, the thin top plate 23, and the bridge 22 will be made to contour to the profile of the back of the person's head, neck and torso. Also, the entire bridge network can also be made of permeable materials to enhance comfort. In addition, the entire bridge network can be made of X-ray penetrable materials.

FIG. 7 is a cross sectional view of the width of the torso being supported by a version of the present invention where it is adapted to support a body in multi or 360 degree directions. Again as before, the base 4 supports vertical members 3 which in turn support members 2 and finally member 2 supports the fabric 5. Down below the body and directly opposite member 2, and attached to the member 3, is a similar functioning and positioned rigid frame member 16.

This rigid frame member 16 supports a separate supporting fabric 28 which is attached to the regular suporting fabric 5. Fabric member 28 is shown slightly slack. However, should the person be rotated 180 degrees, it would function as the original fabric. That is, the rigid frame 16 would be overhead and the slack fabric 28 would become fully tense and provide support to the torso. Likewise, should the person be rotated 90 degrees on his side, he would be supported as in FIG. 2. That is, member 2 and 16 would be over top the torso and they would support fabric members 15 which in turn would support the torso. Although members 15 shown are fabric they can be made of a rigid material as shown in FIGS. 3, 4 and 5 designated as stabilizing members 17. In any direction there is a stabilizing member of either fabric or of a rigid material that prevents side to side movement, as shown in FIG. 2 designated as fabric stabilising member 15 or as shown in FIGS. 3, 4 and 5 designated as rigid stabilizing member 17.

FIG. 8 shows a floating unsupported version of the present invention which supports mainly, the legs, seating area, and lower torso of a person's body. Here the frame 2 outlines the width and length of each supported body portion and also outlines the profile outline of the body in a semi-reclined or seated position. Although no base support structure is shown, it should be apparent that this version of the present invention can be supported on a leg frame like a conventional chair or adapted with wheels, as a wheelchair. It also will become apparent that as with the recumbent version, shown in FIGS. 1, 3, 4 and 5 the frame 2 of FIG. 8 could be adapted to be lowered to a level generally flush with a base surface underneath it for the purposes of facilitating safe and easy horizontal transferring. The backrest 30 is a rigid structure that is padded with a cushioning material. Part of the rigid backrest extends down to form a bridge 29 to span the plane of the torso that is supported by the fabric 5. The arm rest shown 31 is of the conventional type, however the arm rest along with the remainder of the conventional back rest 30 can naturally be designed with the entire concept of the present invention.

FIG. 9 shows a front sectional view of the seat section of FIG. 8, that is, where the observer is face to face with a person that would be seated in the seat of FIG. 8. The fabric 5 supporting the lower thighs is designated by #32, the fabric 5 supporting the outline of the buttocks is designated by #33. Normally the fabric is contoured around each side of the supported body portions as it is around the thighs and the sides and back of the buttocks. As described in the summary of the invention the support fabric applies constant pressure to the sides of the body and therefore would not be appropriate to have the fabric apply pressure to the genital area. To eliminate the pressure against the genitals instead of the fabric extending across the genital area 34, it is tailored to loop below that area and no pressure is applied there. However, the front lower curve of the buttocks below the genital area is still supported by the tensile curving fabric. The result is, besides support from underneath, all of the outside and inside sides of the thighs are supported, all of the right and left sides and the back of the buttocks are supported and most of the front side of the buttocks is supported. A contoured padded bridge 38 spanning the middle concave curve of the buttocks can be attached there in order to improve support in that area.

Figure 10:
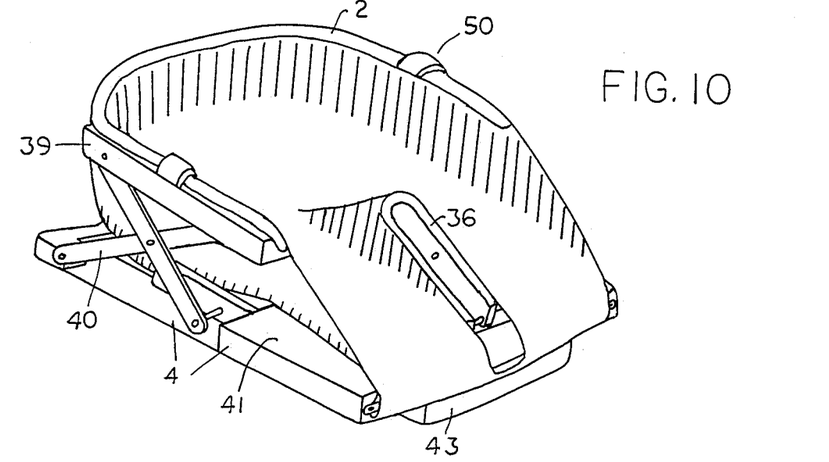
FIG. 10 is a perspective view of a portable, size adjustable, seat version mainly for wheelchair users.

FIG. 10 is a perspective view of a portable size adjustable, seat version of the present invention. It is primarily made for parapelegics and quadrapeligics who have their own wheelchairs. The base 4 supports cross-shaped members 40 which supports channel member 39 and that in turn supports the fabric support frame 2. The fabric supporting member between the legs 36 is elevated to a lower level than fabric supporting frame 2 in order to prevent pressure on the genitals. The supporting contoured fabric is attached to the frame 2 which abuts the right and left sides of the buttocks and also abuts the back of the buttocks. From the frame 2 the fabric 5 extends down, curves inward and under and curves up simultaneously all as one coextensive material towards the front of the seat, curving up, highest to the center member 36 and being attached there, and curving up slightly under the thighs and in front of the buttocks and over a higher section of the base surface 41 and finally being attached to the front of the seat. Varying the distance between the middle member 36 and the back section of member 2, for fitting purposes, is accomplished by unlocking member 50 and adjusting appropriately and then locking it in place. As with the previous versions of this invention the fabric support frame 2 can be lowered to a position generally flush with the base surface 4. In this example instead of using a hydraulic system to lift the frame vertically, as in FIG. 1, a scissor jack type mechanism is used.

FIG. 11 shows the sectional view of the profile of a person sitting in the seat of FIG. 10, with the legs removed. This figure shows the line of support, between the legs, curving downwards from member 36, under and curving up to the fabric support frame 2. As mentioned before, in FIG. 8, the fabric supports from underneath and all of the outside side area of the buttocks and also supports most of the front side area of the buttocks without applying pressure to the genital area. The thighs are better able to withstand pressure and rest on a padded front section 41 of the base.

Figures 12, 13:
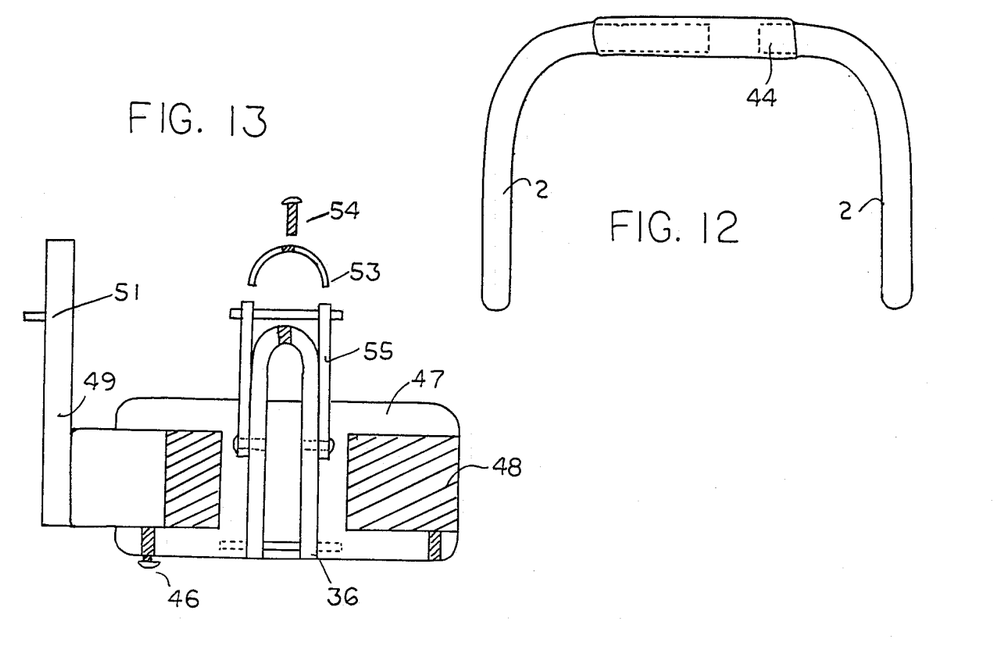
FIG. 12 is a plan view of the fabric supporting frame of the seat version shown in FIG. 10.
FIG. 13 is a partial plan view of the size adjusting and scissor jack lifting mechanizm of the seat in FIG. 10.

FIG. 12 shows of a way to adjust the width of the frame member 2, from the seat of FIG. 10, to fit the width of a person's buttocks. The frame member 2 on one side would be permanently fitted to a side of tube 44, on the other side member 2 would be slidable in and out in tube member 44. Member 2 can easily be adapted to a single or double hip amputee, by having the fabric supporting frame 2 come around the front of the seated person's waist and be attached to the middle member 36.

FIG. 13 shows the adjustment mechanism to vary the spacing between the pair of cross-shaped support members 40, of FIG. 10. A push plate 47 is used to move the cross-shaped members 40 and member 36 to the elevated position. On both sides of the push plate 47 are channels 48. In these channels sit the push bar members 49. The push bar members 49, (only one side shown), can be adjusted to the width of an individual by loosening adjustment screw 46 and moving the push bar 49 to the correct place and then retightening the adjustment screw 46. Near the back end of the push bar 49 is the pin 51 which enters one member of the cross shaped members 40. Likewise, member 36 acts as one unit of a cross-shaped members. Attached to member 36 are rigid members 55 which act as the second member of a cross-shaped scissor type mechanism. However, due to its shorter length member 55 never extends above member 36 and members 36 and 55 do not take on a true cross-shaped appearance. The push plate 47 is drawn about an inch and a half towards the back of the seat thereby raising the outside pair of cross-shaped members 40 and inside member 36 to their appropriate elevated position and down again whenever patient transferring is needed. Many mechanisms are available to move the push plate 47 back and forth, such as, electro-mechanical, hydraulic, lever type systems, crank type systems, and the like.

Also in FIG. 13 is shown the method of attachment of the support fabric 5 to member 36. The support fabric 5 of FIG. 10 is placed between the tip of member 36 and a curved, fabric sandwich plate 53. A screw 54 is passed through a hole in the curved sandwich plate 53, and through a hole in the support fabric and finally into a threaded hole in member 36 and tightened there to keep the fabric in place.

What is claimed is:

1. An individually fitted apparatus for supporting a body, whereby pressure is redistributed from underneath body portions and onto the substantial side area of the lengthwise and widthwise sides of said body portions, providing maximum support contact area and optimal reduction and uniformity in support pressure, the said apparatus comprising in combination;

a frame member made of rigid tubular material that is supported and elevated by rigid vertical members, and adapted to be located above and adjacent to but not in contact with said body portions, with the said frame member adapted to extend the length and width of said body portions, a fabric, anatomically and coextensively tailored to deeply and tightly fit a three-dimensional profile of the width and length of said body portions, and adapted to extend the length and width of said body portions, a top end of the said fabric that is tailored to oppose the vertical side of said body portions is attached to the said frame, the said fabric supported from said frame is adapted to extend down a side of said body portions, curve down the said side of the body portions, pass under body portions, curve and extend up the other side of said body portions, and is attached to the said frame, similarly as the said first side, the said fabric supporting the said body portions in a deep tight three-dimensional contour, the said frame and said fabric together are dimensioned to support and suspend the said body portions, using said vertical members, a rigid bridge member is attached to said fabric to support only the concave or planarly body surface areas, the said bridge member having a contoured, undulated surface to conform to said concave or planarly body surface areas, the surface of the said bridge and said fabric that is in contact with the said planar or concave body portions is padded, by placing a body portion in the said apparatus, the said fabric tenses and the said fabric adapted to contact the sides of the said body portions moves inwardly against the said sides of said body portions with a force or a pressure directly proportional to the weight of the said body portions being supported, this dynamic action redistributes the support pressure from underneath the body portions and onto the sides of the body portions, thus substantially reducing the effect of gravity.

2. The apparatus of claim 1, in which the said frame is adapted to rest generally flush with a base surface for the purposes of allowing horizontal patient transferring onto and off the apparatus, and including lifting means adapted to move said frame vertically to support and suspend said body portions.

3. The apparatus of claim 1, in which the said frame and said fabric, and said bridge, support all said body portions of an individual in a recumbent position.

4. The apparatus of claim 1, in which the said frame, said fabric, and said bridge is adapted to support an individual in a reclined position.

5. The apparatus of claim 1, in which the said frame is adapted to be located adjacent to the right, left, and back sides of a seated individual's buttocks, and the said frame, also, is adjacent to the area, between the legs, and below the groin area of the said individual's buttocks, the said fabric, attached to the said frame, abuts the right, left, and back sides of the said individual's buttocks, the said fabric attached to said frame between the legs and below the groin area, itself abuts the front side area below the groin area of the said individual's buttocks.

* * * * *